(12) United States Patent
Klaes

(10) Patent No.: US 8,397,986 B1
(45) Date of Patent: Mar. 19, 2013

(54) AUTOMATICALLY LOADING MEDICAL DATA CARD

(76) Inventor: Steven Klaes, Mayville, WI (US)

( * ) Notice: Subject to any disclaimer, the term of this patent is extended or adjusted under 35 U.S.C. 154(b) by 112 days.

(21) Appl. No.: 12/851,599

(22) Filed: Aug. 6, 2010

Related U.S. Application Data

(60) Provisional application No. 61/232,418, filed on Aug. 8, 2009.

(51) Int. Cl.
*G06K 5/00* (2006.01)
(52) U.S. Cl. ............ 235/380; 235/487; 235/375; 705/2; 705/3
(58) Field of Classification Search .................. 235/380, 235/492, 487, 451, 375; 705/2–4
See application file for complete search history.

(56) References Cited

U.S. PATENT DOCUMENTS

| | | | |
|---|---|---|---|
| 2004/0038389 A1* | 2/2004 | Maus et al. ................ | 435/287.2 |
| 2005/0240613 A1* | 10/2005 | Logan, Jr. .................... | 707/102 |
| 2008/0071577 A1* | 3/2008 | Highley .......................... | 705/3 |
| 2009/0271221 A1* | 10/2009 | Aridi et al. ....................... | 705/3 |

\* cited by examiner

*Primary Examiner* — Edwyn Abaze
(74) *Attorney, Agent, or Firm* — Brannen Law Office, LLC

(57) ABSTRACT

According to one aspect of the present invention, the medical data card automatically runs when inserted into a communication port of a computer. One type of communication port can be a USB port. The card prompts the service provider to enter a password that is verified by the server. The patient ID can then be entered and the patient's records can be retrieved. The server can be remotely accessed by the healthcare provider via the internet. A log is generated and stored on the server containing information such as who, when, what records were accessed. A family card can be provided permitting a minor's records to be obtained via the parent's or guardian's card. The card and the server automatically synchronize each time the card is used.

17 Claims, 1 Drawing Sheet

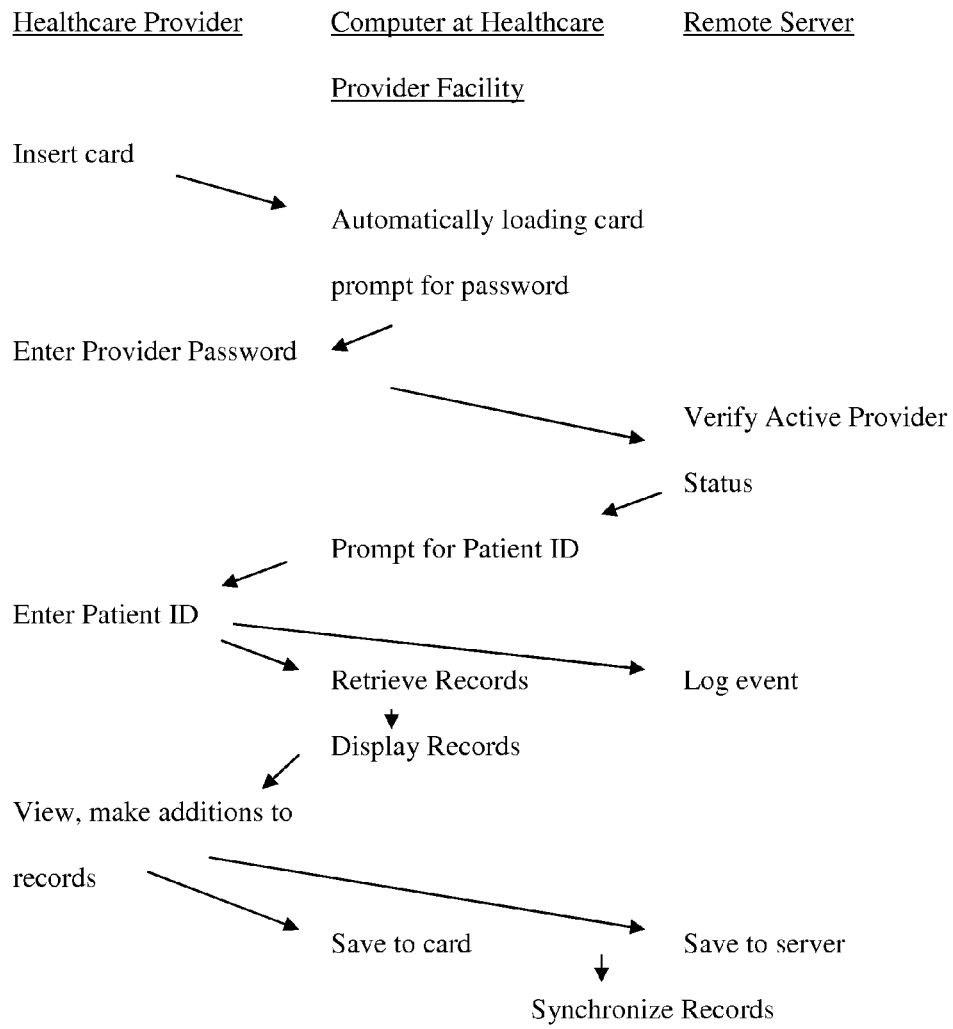

US 8,397,986 B1

AUTOMATICALLY LOADING MEDICAL DATA CARD

This application claims priority on copending United States provisional patent application filed on Aug. 8, 2009 and having application No. 61/232,418, wherein the entire contents of which is hereby incorporated herein by reference.

BACKGROUND OF THE INVENTION

1. Field of the Invention

The present invention relates to an automatically loading medical data card, and specifically the use of cards that are accessible without specialized software stored on a host computer.

2. Description of the Related Art

There are many portable media devices that can be used to store medical data. Among the many privacy concerns is the unauthorized access to data stored on the cards.

Further, the use of medical data cards in contingent upon the ability of the healthcare provider being able to quickly, verifiably, and efficiently navigate the health records.

Still further, there are logistical issues involved with installing and maintaining specialized software on the healthcare provider's computers. Installing software onto a facility's computers is time consuming, expensive and may not be done in all locations and on all computers.

Thus there exists a need for an automatically loading data card that solves these and other problems.

SUMMARY OF THE INVENTION

According to one aspect of the present invention, the medical data card automatically runs when inserted into a communication port of a computer. One type of communication port can be a USB port. The card prompts the service provider to enter a password that is verified by the server. The patient ID can then be entered and the patient's records can be retrieved. The server can be remotely accessed by the healthcare provider via the internet. A log is generated and stored on the server containing information such as who, when, what records were accessed.

According to one advantage of the present invention, the card contains software to automatically load when inserted into the communication port of the computer. In this regard, there is no need to preload any type of software on the healthcare provider facility computer. This ensures that all computers having an internet connection will have access to the patient's medical records.

According to another advantage of the present invention, data logs are generated detailing who accessed the patient's records, when the access was granted, and what changes or additions were made each time the data was accessed.

According to another advantage of the present invention, the patient can restrict who has access to the records in non-emergency situations. Further, certain medical records can be redacted in non-emergency situations. For example, if a doctor is accessing records pertaining to arthritis, there may be little reason for that doctor to have access to past medical records for treatment of hair loss.

According to a further advantage of the present invention, a family card can be provided wherein access to a child's records can be accessed through a parent's or guardian's card.

According to a still further advantage yet of the present invention, records can be synchronized between the card and the server. This ensures that if ever records are not immediately uploaded to the server, that the records will be updated the next time that the card is in communication with the server.

Other advantages, benefits, and features of the present invention will become apparent to those skilled in the art upon reading the detailed description of the invention and studying the drawings.

BRIEF DESCRIPTION OF THE DRAWINGS

FIG. 1 is a flow chart showing the process of obtaining medical records using the present invention.

DETAILED DESCRIPTION OF THE PREFERRED EMBODIMENTS

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

A flowchart showing the logic of the present invention is illustrated in FIG. 1. This flowchart shows one preferred process for obtaining medical information about a patient using an automatically loading medical data card.

In the preferred embodiment, the medical data card has length and width dimensions similar to those of a credit card. At one end of the card is an attachment for connecting to a USB communication port of a computer. The USB drive can be located at one side or be centrally located at one end of the card. The card port is preferably dual sided; i.e. can be inserted into a USB port either up-side down, or down-side down. In an alternative embodiment, the card can wirelessly communicate with the host computer.

The card contains a piece of software or script that automatically runs when the card is first placed in communication with the computer. The program preferably puts itself into a loop that runs a predetermined number of times. The program views all of the drives on the computer, seeking a removable drive that is not a diskette reader. Once a drive is located, a search is performed for a file consisting of a predetermined name.

Once the file with the predetermined name is located, the card determines which type of computer and which operating system is being run on the computer. If the .Net Framework is not installed, the card automatically installs the software onto the computer. If the .Net Framework is located (by checking the registry entries), then this step is skipped and the program can be started.

Turning now to FIG. 1, a flowchart showing operation in a healthcare facility setting is described. The healthcare provider first loads the card into the facility computer. The card automatically runs (without the need for any user prompting or specialized software being on the host computer) and prompts the healthcare provider for the provider password.

The healthcare provider enters his or her provider password, and the card program automatically accesses the server via an internet connection and verifies that the healthcare provider has an active provider status. The patient can assign a priority to selected healthcare providers and restrict access to certain types of information based on the assigned priority.

The program then prompts the healthcare provider to enter the patient ID (which can be transmitted in advance of the patient's arrival at the facility). Upon entering the patient ID, the card program retrieves and then displays the patient records. A log entry is recorded on the server detailing who accessed the patient's records, the day and time of the data access, and what, if any, changes or additions were made by the healthcare provider.

The changes can be saved to the card and the server at the same time.

It is also understood that the card and the server synchronize each time that the card is in communication with the server.

According to another aspect of the present invention, a family card can be provided wherein minor children or dependents (or anyone for that matter) can be linked to the cardholder electronically to allow access to the secondary person's records via the first person's card. This would advantageously allow for access to a child's records through their parent's cards. In this regard, the parent's patient card can determine when the minor children remain minors and can disallow access to the children's card when the child reaches a predetermined age, such as 18.

Permissions can be set detailing who has access to what information, if any.

Thus it is apparent that there has been provided, in accordance with the invention, an automatically loading medical data card that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A method of retrieving medical data comprising the steps of:
   providing a computer with a data port;
   providing a patient card that can communicate with the computer via the data port;
   providing a patient having a patient identification;
   populating the patient card with medical information regarding the patient;
   providing minor children;
   populating the card of a parent with information regarding the minor children of the parent;
   determining the date that the minor children reach the age of 18;
   deleting all information regarding the minor children upon the date that the minor children reach the age of 18;
   providing a medical professional and assigning a medical professional password to the medical professional;
   running a program contained on the card to cause the computer to prompt the medical professional for the medical professional password; and
   having the medical professional retrieve the medical information regarding the patient.

2. The method of claim 1 wherein:
   the step of providing a computer with a data port comprises the step of providing a computer with a USB port; and
   the step of providing a patient card that can communicate with the computer via the data port comprises the step of inserting the patient card into the USB port.

3. The method of claim 1 wherein:
   the step of providing a computer with a data port comprises the step of providing a computer with a wireless communication port; and
   the step of providing a patient card that can communicate with the computer via the data port comprises the step of wirelessly communicating with the wireless communication port.

4. The method of claim 1 wherein the method of assigning a medical professional password to the medical professional comprises assigning a medical professional password that can is unrestricted by the location of the healthcare professional and further comprising the step of authenticating the medical professional password before allowing access to the patent medical information.

5. The method of claim 1 wherein the step of having the medical profession retrieve medical information regarding the patient comprises retrieving the medical information regarding the patient from the card.

6. The method of claim 1 further comprising the step of providing a server, wherein the server authenticates the healthcare provider password prior to allowing access to the medical information regarding the patient.

7. The method of claim 6 wherein the step of having the medical profession retrieve medical information regarding the patient comprises retrieving the medical information regarding the patient from the server.

8. The method of claim 1 wherein the step of running a program contained on the card to cause the computer to prompt the medical professional for the medical professional password is accomplished without the need for any type of preloaded software on the computer.

9. The method of claim 1 further wherein:
   the computer has a certain type of operating system; and
   the step of running a program contained on the card to cause the computer to prompt the medical professional for the medical professional password comprises the step of running a code on the card to determine which type of operating system is on the computer, and then automatically running a program on the card that is compatible with the determined operating system.

10. The method of claim 1 further comprising the step of creating a data log comprising every time medical information regarding the patient is accessed.

11. The method of claim 1 further comprising the step of providing a server and further comprising the step of creating a data log on said server recording information about when and whom accessed medical information regarding the patient.

12. The method of claim 1 further comprising the step of allowing the patient to prioritize their medical information and to assign priority to particular healthcare providers in order to restrict access based on the assigned priority.

13. The method of claim 1 further comprising a server containing medical information regarding a patient, and wherein the medical information regarding a patient is synchronized on the card and on the server each time the card is utilized by a healthcare professional.

14. The method of claim 1 wherein the step of providing a card comprises the step of providing a card that is approximately the size of a credit card.

15. A method comprising the steps of:
   providing a computer with a data port;
   providing a server that remotely communicates with the computer;
   providing a patient card that can communicate with the computer via the data port;
   providing a patient having a patient identification and having medical information regarding the patient;
   providing minor children;
   populating the card of a parent with information regarding the minor children of the parent;
   determining the date that the minor children reach the age of 18;

deleting all information regarding the minor children upon the date that the minor children reach the age of 18;

providing a medical professional and assigning a medical professional password to the medical professional;

running a program contained on the patient card to cause the computer to prompt the medical professional for the medical professional password;

having the server authenticate the medical professional password;

having the medical professional enter the patient identification; and having the medical professional retrieve the medical information regarding the patient.

16. The method of claim 15 further comprising the step of populating the patient card with medical information regarding the patient, wherein the step of having the medical professional retrieve medical information regarding the patient comprises retrieving the medical information from the card.

17. The method of claim 15 wherein the step of providing a computer with a data port comprises the step of providing a computer with a USB port.

* * * * *